(12) United States Patent
Asiyanbola et al.

(10) Patent No.: US 8,908,949 B2
(45) Date of Patent: Dec. 9, 2014

(54) METHOD OF DETECTING FOREIGN BODIES

(75) Inventors: Bolanle Asiyanbola, Baltimore, MD (US); Ralph Etienne-Cummings, Baltimore, MD (US); Chao-Cheng Wu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 324 days.

(21) Appl. No.: 13/580,448

(22) PCT Filed: Feb. 22, 2011

(86) PCT No.: PCT/US2011/025759
§ 371 (c)(1), (2), (4) Date: Jan. 18, 2013

(87) PCT Pub. No.: WO2011/103590
PCT Pub. Date: Aug. 25, 2011

(65) Prior Publication Data
US 2013/0136323 A1 May 30, 2013

Related U.S. Application Data

(60) Provisional application No. 61/306,696, filed on Feb. 22, 2010.

(51) Int. Cl.
G06K 9/00 (2006.01)
G06K 9/62 (2006.01)

(51) Int. Cl.
(52) U.S. Cl.
CPC .............. *G06K 9/00577* (2013.01); *A61B 6/12* (2013.01); *G06F 19/3406* (2013.01); *G06T 7/0014* (2013.01); *G06F 19/3443* (2013.01); *G06F 19/3475* (2013.01); *G06T 2207/10088* (2013.01); *G06T 2207/10116* (2013.01); *G06T 2207/10132* (2013.01); *G06T 2207/30004* (2013.01)
USPC ........... 382/130; 382/128; 382/131; 382/132; 382/133; 382/209

(58) Field of Classification Search
CPC ........... A61B 19/5244; A61B 19/5212; A61B 2019/5289; A61B 2019/5265; A61B 2019/502; A61B 2019/5276; A61B 6/12; A61B 6/032; A61B 2019/524; A61B 2019/5295; A61B 6/4258; G06K 9/3241; G06T 2207/10132; G06T 7/0038; G06T 2207/10081; G06T 2207/10116
USPC .................................................. 382/128–134
See application file for complete search history.

(56) References Cited

U.S. PATENT DOCUMENTS

2007/0237372 A1* 10/2007 Chen et al. ..................... 382/128
2008/0262345 A1* 10/2008 Fichtinger et al. ............ 600/426

FOREIGN PATENT DOCUMENTS

| JP | 04-038933 A | 2/1992 |
| JP | 06-038980 A | 2/1994 |

(Continued)

OTHER PUBLICATIONS

Cima, R., et al., "Incidence and characteristics of potential and actual retained foreign object events in surgical patients", J Am Coll Surg 2008; 207:80-87.

(Continued)

*Primary Examiner* — Amir Alavi
*Assistant Examiner* — Kenny Cese
(74) *Attorney, Agent, or Firm* — Johns Hopkins Technology Transfer

(57) ABSTRACT

A system for detecting post-operative retained foreign bodies has a data storage unit adapted to receive and store a reference image of a surgical object, and a data processor in communication with the data storage unit. The data processor is configured to receive an image of an internal region of a patient and to receive the reference image from the data storage unit, and the data processor is configured to perform operations based on an algorithm to compare the reference image to at least a portion of the image of the internal region of the patient and determine whether a retained foreign body is present in the patient.

20 Claims, 6 Drawing Sheets

(51) Int. Cl.
*A61B 6/12* (2006.01)
*G06F 19/00* (2011.01)
*G06T 7/00* (2006.01)

(56) References Cited

FOREIGN PATENT DOCUMENTS

| | | |
|---|---|---|
| JP | 2006-122321 A | 5/2006 |
| KR | 10-2000-0024872 A | 5/2000 |

OTHER PUBLICATIONS

Gawande, A., et al., "Risk factors for retained instruments and sponges after surgery", N Engl J Med, 2003; 348:229-235.

Kaiser, C., et al., "The retained surgical sponge", Ann Surg, 1996; 224:79-84.

Gibbs, V., et al., "Preventable errors in the operating room: retained foreign bodies after surgery—Part I", Curr Probl Surg, 2007; 44:281-337.

* cited by examiner

METHOD OF DETECTING FOREIGN BODIES

CROSS-REFERENCE TO RELATED APPLICATIONS

This application is a 35 U.S.C. §371 U.S. national entry of International Application PCT/US2011/025759 having an international filing date of Feb. 22, 2011, which claims the benefit of U.S. Provisional Application No. 61/306,696, filed Feb. 22, 2010, the content of each of the aforementioned applications is herein incorporated by reference in their entirety.

BACKGROUND

1. Field of Invention

The field of the currently claimed embodiments of this invention relates to systems and methods of detecting retained foreign bodies, and more particularly systems and methods of detecting foreign bodies retained in a patient during or after surgery.

2. Discussion of Related Art

Objects used during surgery can be unintentionally left in the patient. Such a retained foreign body (RFB) in which an object is left in a patient after surgery is a rare event. The incidence rates of RFBs are reported in the range of 1 RFB per 5500 operations for RFBs detected peri operatively and 1 RFB per 9000 operations to 1 per 19,000 for RFBs detected postoperatively. Though rare, RFBs can cause a number of serious complications, such as prolonged operating time, abscess formation, and death.

The consequences of failing to detect RFBs have been well studied, as is described in the following examples:

Cima R R, Kollengode A, Garnatz J, et al. Incidence and characteristics of potential and actual retained foreign object events in surgical patients. *J Am Coll Surg* 2008; 207:80-87.

Gawande A A, Studdert D M, Orav E J, et al. Risk factors for retained instruments and sponges after surgery. *N Engl J Med* 2003; 348:229-235.

Kaiser C W, Friedman S, Spurling K, Pfeifer R. The retained surgical sponge. *Ann Surg* 1996; 224:79-84.

Gibbs V C, Coakley F D, Reines H D. Preventable errors in the operating room: retained foreign bodies after surgery—Part I. *Curr Probl Surg* 2007; 44:281-337.

However, the process of detecting RFBs has not been adequately studied. The process of detection includes factors contributing to the decision to prolong the search for RFBs, the labor (or steps) expended to search for RFBs, and the time it takes to look for RFBs.

Nonetheless, due to the serious consequences and liability issues, the search for RFBs has an impact on each and every surgery performed. Consequently, the process of detection is arguably larger in scope today than in the past due to having to detect rare occurrences in a high volume of data. Current proposed and prior art technologies include automated data identity capture (ADIC) methods (e.g. bar codes and RFID tags). However, such prior art can only be used to detect sponges. Further, they do not decrease the need for x-rays because in 81% of cases, x-rays are taken to identify RFBs independent of sponge count results. In other words even if one uses ADIC technology one would still have to take an x-ray in 81% of cases as such using ADIC technology would not only prolong the process of looking for RFBs but would also necessitate an X-ray because not all RFB are detected with ADIC technology. Further ADIC does not address the problem of only a part of an instrument being lost as of now such parts can only been seen with X-ray. Therefore, such approaches are not widely accepted and currently manual counting and x-ray methods are the standard of care. However, the standard of care has its limitations as well: up to 20% of positive x-rays are read as falsely negative and the accuracy of radiologists' determination of RFBs decreases as the size of the RFB decreases so that RFBs less than 10 mm in length have an only 30% chance of being detected by radiologists. There thus remains a need for improved methods and systems for detecting RFBs.

SUMMARY

A system for detecting post-operative retained foreign bodies according to an embodiment of the current invention has a data storage unit adapted to receive and store a reference image of a surgical object, and a data processor in communication with the data storage unit. The data processor is configured to receive an image of an internal region of a patient and to receive the reference image from the data storage unit, and the data processor is configured to perform operations based on an algorithm to compare the reference image to at least a portion of the image of the internal region of the patient and determine whether a retained foreign body is present in the patient.

An automated method of detecting post-operative retained foreign bodies according to an embodiment of the current invention includes storing a reference image of a surgical object in non-transient, digital form; obtaining an image of an internal region of a patient in digital form; retrieving the reference image and comparing, based on a computer algorithm, the reference image to at least a portion of the image of the internal region of the patient; and determining whether a retained foreign body is present in the patient based on the comparing the reference image of the surgical object to the at least a portion of the image of the internal region of the patient using the computer algorithm on a computer.

A computer-readable medium according to an embodiment of the current invention includes software, when executed by a computer, the software causes the computer to receive an image of an internal region of a patient; receive a reference image of a surgical object; compare the reference image to at least a portion of the image of the internal region of the patient using a computer algorithm; and determine whether a retained foreign body is present in the patient based on the comparing the reference image of the surgical object to the at least a portion of the image of the internal region of the patient using the computer algorithm.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
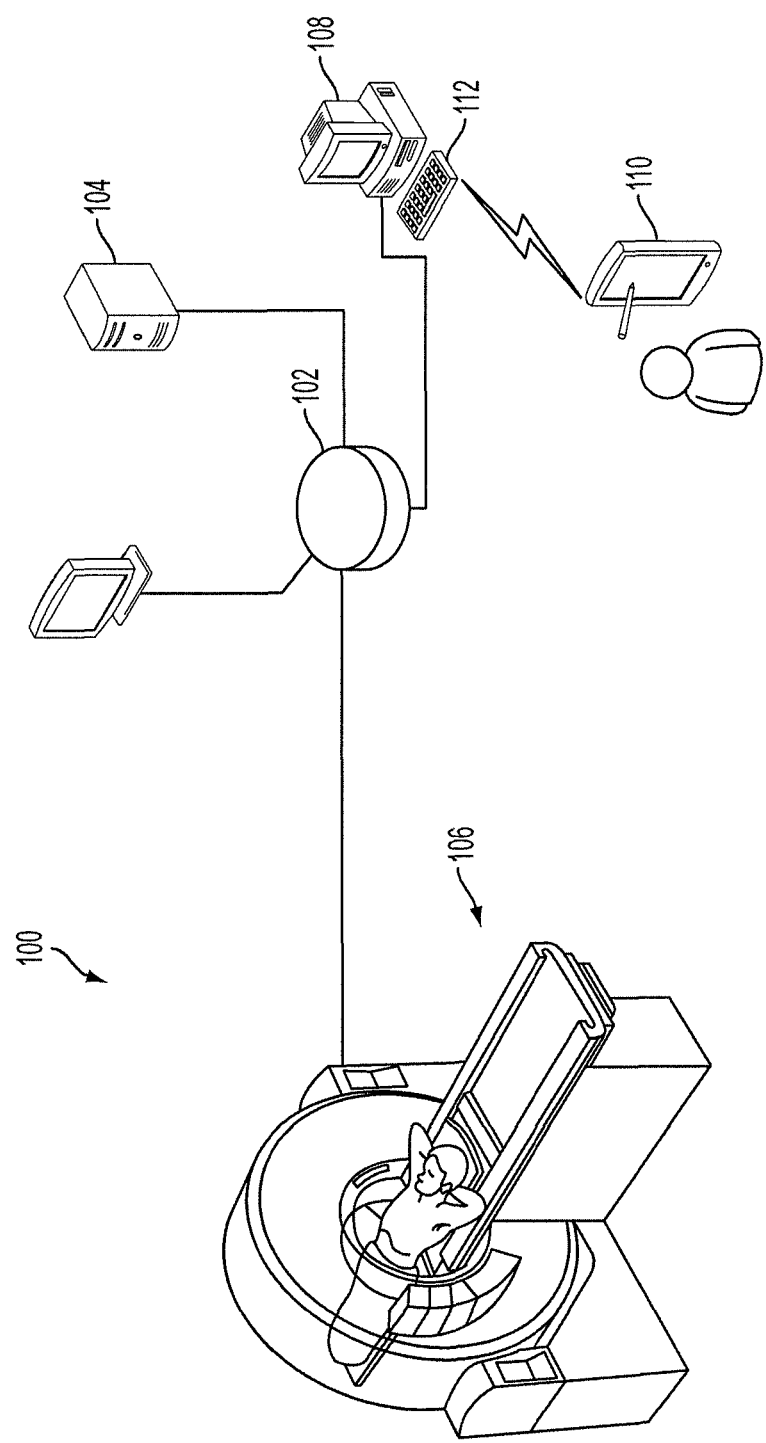
FIG. 1 is a schematic illustration of a system for detecting post-operative retained foreign bodies according to an embodiment of the current invention.

A system 100 for detecting post-operative retained foreign bodies (RFBs) according to an embodiment of the current invention is illustrated schematically in FIG. 1. The system 100 includes a data storage unit 102 adapted to receive and store one or more reference images of a surgical object. The data storage unit is in communication with a data processor 104. The data processor 104 is configured to receive an image of an internal region of a patient and to receive the reference image from the data storage unit 102. The data processor 104 is also configured to perform operations based on an algorithm to compare the reference image to at least a portion of the image of the internal region of the patient and determine whether a retained foreign body is present in the patient.

In some embodiments of the current invention, the system 100 can further include an image acquisition system 106 that is in communication with the data processor 104 and/or data storage unit 102. The image acquisition system 106 can be selected from any suitable medical imaging system for the particular application, such as, but not limited to, x-ray systems, CAT scan systems, magnetic resonance imaging (MRI) systems, or ultrasound systems, for example.

The data storage unit 102 and the data processor 104 can be separate components as illustrated in FIG. 1, or they can be portions of a combined component such as a work station, personal computer, laptop computer, tablet or other device depending on the particular application. The data storage unit 102 and data processor 104 can also be distributed over a network, for example, rather than being localized. The network can be, for example, a local area network (LAN), a wide area network (WAN), a wireless network and/or the internet, for example. In addition, personal computer 108 and/or tablet 110 can be used in conjunction with, or in place of, the data storage unit 102 and data processor 104 according to some embodiments of the current invention. Further input and/or output devices can also be included in the system 100, such as, but not limited to, a keyboard 112, a mouse and further image display 114, for example.

The data storage unit 102 can include one or more solid state memory units, hard drives, optical storage such as CDs or DVDs, or other suitable memory devices. The data processor can be the CPU of a computer that includes one or more processors, graphics processors, multiple processors over a network, and/or a special-purpose data processor designed for a particular embodiment of the current invention, for example.

The reference image can be preselected by an expert who has expert knowledge viewing and analyzing images of the particular modality such that it has a characteristic appearance of the surgical object. For example, an expert may select an image of a surgical needle in an x-ray image as being characteristic of the appearance of such an object in such an imaging modality. However, the concepts of the invention are not limited to this particular example. This reference image can be processed, as desired, such as, but not limited to, various types of filtering, edge detection, segmentation, etc. In some embodiments, more than one reference image can be selected by an expert. In further embodiments, one or more reference image can be used for generating further reference images. For example, a reference image may show a surgical object of interest in a side view. The image can then be process to show how the surgical object would be expected to appear if it had been rotated, translated and/or scale in size by various amounts. The plurality of reference images thus provides a template of a surgical object in a number of discrete positions and orientations in which to match with an image of an internal region of a patient. The data processor 104 is configured, for example by programming and/or special purpose electronic components, to determine whether there is a sufficient match between any one or more of the reference images. This process of using a reference image to essentially look for particular surgical objects can greatly reduce computational complexity and time need to perform the processing. Furthermore, utilizing expert knowledge to select a reference allows the system to benefit from expert human knowledge without necessarily having to always have an expert reviewing the data. In some embodiments, the automated detection processing can be performed in real time with the patient still in the operating room, for example. However, the concepts of the current invention are not limited to only real-time processing. The system could also be used for post-procedure processing.

The data processor can also be configured to preprocess the images of the internal regions of the patient, such as by applying various types of filtering, edge detection, segmentation, etc. In addition, the entire images of the internal regions of the patients, or portions of those images, can also be used to generate a plurality of images, for example by applying rotational, translational and/or scaling transformations. Such pluralities of images can then be compared to each one or more reference image by the matching algorithms of the data processor 104 in some embodiments of the current invention.

In some embodiments, the surgical object can be one or more surgical sponge, surgical tool, and/or part of a surgical tool, for example. The surgical object can also be one or more surgical objects that were used during surgery, but were not included in the predefined surgical pack for the surgery. Examples of some possible surgical tools include, but are not limited to, needles, scalpels, clamps, forceps, retractors, needle holders, electro-cautery components, and electrical leads. More generally, any foreign body of interest can be the subject of the detection.

Another embodiment of the current invention is directed to an automated method of detecting post-operative retained foreign bodies. The method according to this embodiment of the current invention includes storing a reference image of a surgical object in non-transient, digital form; obtaining an image of an internal region of a patient in digital form; retrieving the reference image and comparing, based on a computer algorithm, the reference image to at least a portion of the image of the internal region of the patient; and determining whether a retained foreign body is present in the patient based on the comparing the reference image of said surgical object to the at least a portion of the image of the internal region of the patient using the computer algorithm. In some embodiments, this method can be performed using the system 100 described above. However, this embodiment of the current invention is not limited to being performed only using the system 100.

Another embodiment of the current invention is directed to a computer-readable medium comprising software. When the software is executed by a computer, it causes the computer to receive an image of an internal region of a patient, receive a reference image of a surgical object, compare the reference image to at least a portion of the image of the internal region of the patient using a computer algorithm, and determine whether a retained foreign body is present in the patient based on the comparing the reference image of the surgical object to the at least a portion of the image of the internal region of the patient using the computer algorithm. The software can be executable on the system 100 according to some embodiments of the current invention. However, this embodiment of the current invention is not limited to being executed only on the system 100.

EXAMPLES

The following example is an application of some specific embodiments of the current invention. It is not intended to limit the general scope of the invention, which is defined by the claims.

Modified Map-Seeking Circuits

An embodiment of the current invention includes computer aided detection (CADe) to assist in the detection of RFB with machine learning techniques. We utilized a modified map seeking circuit in this example.

Figure 2A:
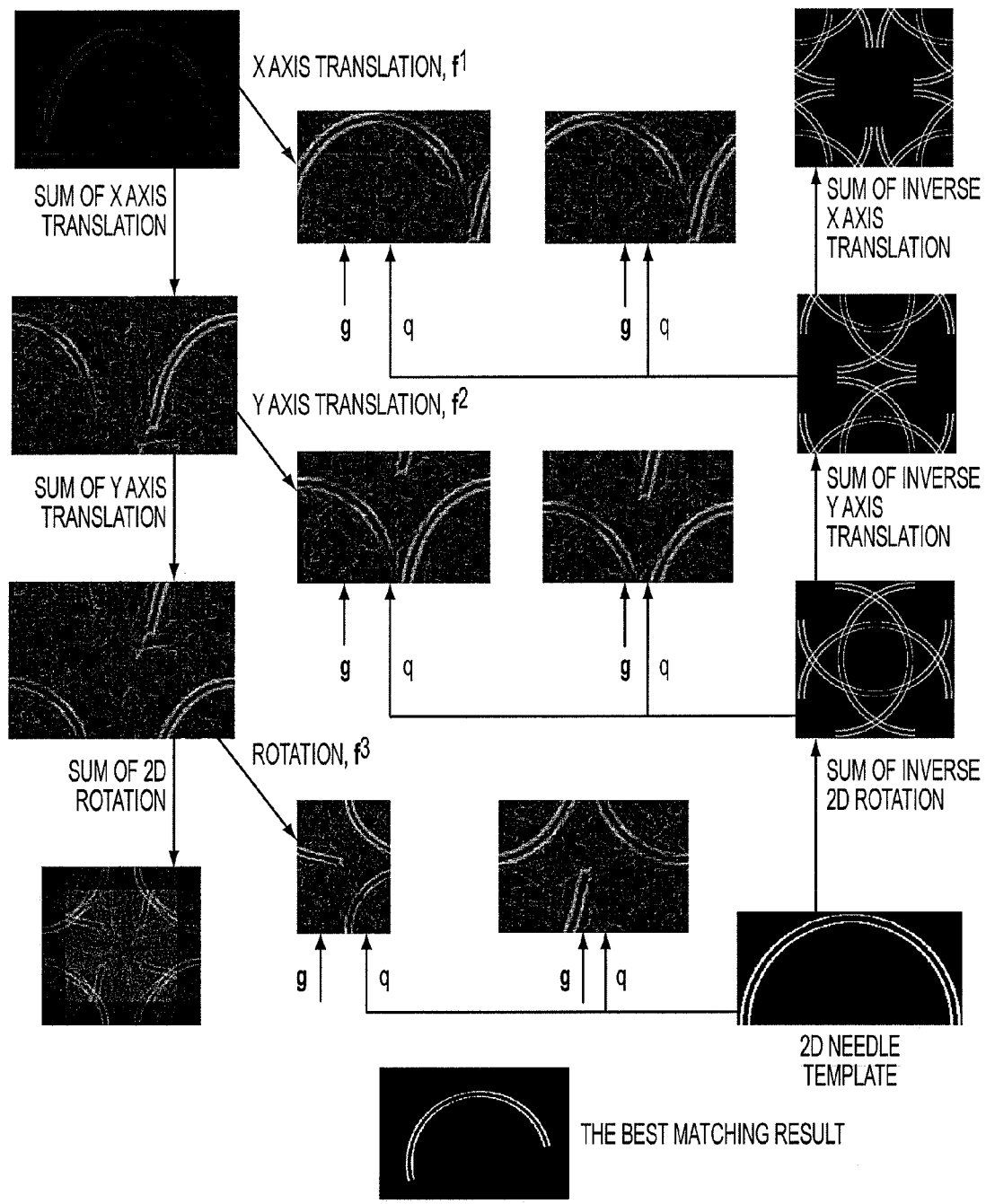
FIG. 2A is a needle matching example of using a Map-Seeking Circuit Algorithm according to an embodiment of the current invention.
Figure 2B:
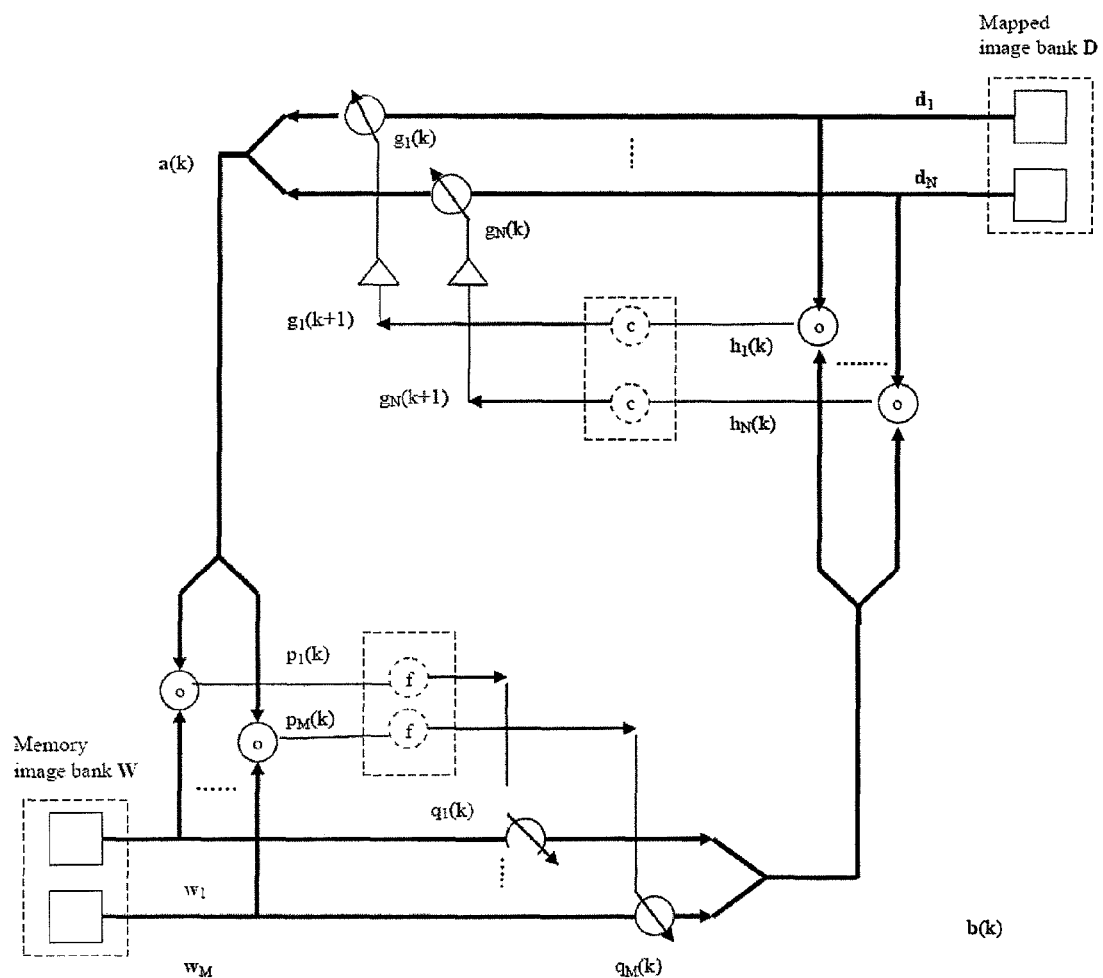
FIG. 2B is a schematic illustration of a Map-Seeking Circuit Algorithm according to an embodiment of the current invention.

Given an input image and a template image, the goal of pattern recognition is to find the template image with a composition of transformations which gives the best fit in the inputted image. The transformations are restricted to be able to decompose into an independent and finite product, where each term in the product is a linear transformation on the space of image. In our case, the example of the two-dimensional needle matching needs to consider the product of rotation, translations, and scale. Assuming each component transformation is discrete and finite, then this problem can be solved by a brute-force search of the entire transformation space as follows, $$T = T_{iL}^{(L)} \circ \ldots \circ T_{il}^{(l)} \circ \ldots \circ T_{i2}^{(2)} \circ T_{i1}^{(1)}$$

where $1 \leq i_l \leq n_l$ for $l=1, \ldots, L$. The entire transformation space would require the evaluation of $n_1 n_2 \ldots n_L$ transformations. The number of evaluation becomes unfeasible for most real-world applications. The major contribution of map-seeking circuits is to exploit an iterative algorithm which makes the transformations which could be imbedded in a framework by using superposition. With the superposition, the number of evaluations is reduced to the sum of each component transformation, $n_1 + n_2 + \ldots + n_L$. An example to implement the MSC to find a needle inside patient's X-ray image is shown in FIG. 2. FIG. 2 shows three transformations, horizontal translations, vertical translations, and 2D rotations. The transformation functions and weighting parameter in FIG. 2 are calculated based on the following equations:

$$f^m = \sum_{j=1}^{m} g_j^m \cdot r_j^m (f^{m-1})$$

$$b^m = \begin{cases} \sum_{j=1}^{m} g_j^m \cdot r_j^{\prime m}(b^{m+1}) & \text{for } m = 1 \ldots L \\ \sum_{k} z \langle w_k, f^L \rangle \cdot w_k & \text{for } m = L+1 \end{cases}$$

$$q_i^m = \langle r_i^m(f^{m-1}), b^{m+1} \rangle$$

$$g^m = \max\left[0, g_i^m - k_1 \cdot \left[1 - \frac{q_i^m}{\max q^m}\right]^{k_2}\right]$$

where $f^m$ is the forward transformation, $b^m$ is the backward transformation, $q_i^m$ is the correlation between the transformed inputted image and template image, and $g^m$ provides the weighting parameter for the next iteration. The weighting parameter, $g^m$, would be adjusted to reflect the best fit transformation. Due to the iterative design of Map-Seeking Circuits, the weighting parameter should converge to 1 after a few iterations.

The map-seeking circuit provides a nice solution to match a needle if there is one in the patient's image. It has proven to be very effective to find the best transformations of the template image with proportional computational complexity. However, in our case, our concern is whether or not there is a needle in a certain region of the patients' X-ray image. The exact transformations of a needle are not our concern. The solution we would need is to exploit the weighting parameter, $g^m$, against a threshold to make a hard decision for needle detection. Nevertheless, detecting whether or not needles present in the whole X-ray image does not assist a doctor with finding the missing needles. To provide which small region has a higher probability of containing a missing needle, the X-ray image would need to be segmented into several small pieces. This process introduces a new problem to the original map-seeking circuits. In this example, we introduce a reference image which would provides a global max q for the weighting parameters, $g^m$ as follows.

$$g^m = \max\left[0, g_i^m - k_1 \cdot \left[1 - \frac{q_i^m}{\max q^{Ref}}\right]^{k_2}\right]$$

The reference image not only provides a global maximum q, but also has several advantages. First, it introduces a doctors' knowledge to the algorithm to increase the detection rate. The doctors' knowledge can be introduced to the algorithm because the needle in the reference image picked by doctors would be used as the global maximum against other inputted images. Second, with the reference image, the weighting parameter, $g^m$, could be seen as a probability of a needle presented in the inputted images compared to the reference image. Third, the reference reduces the number of iterations the original MSC requires for convergence. Normally, only two iterations are good enough with the reference image due to the global maximum q.

Experiments

Figure 3A:
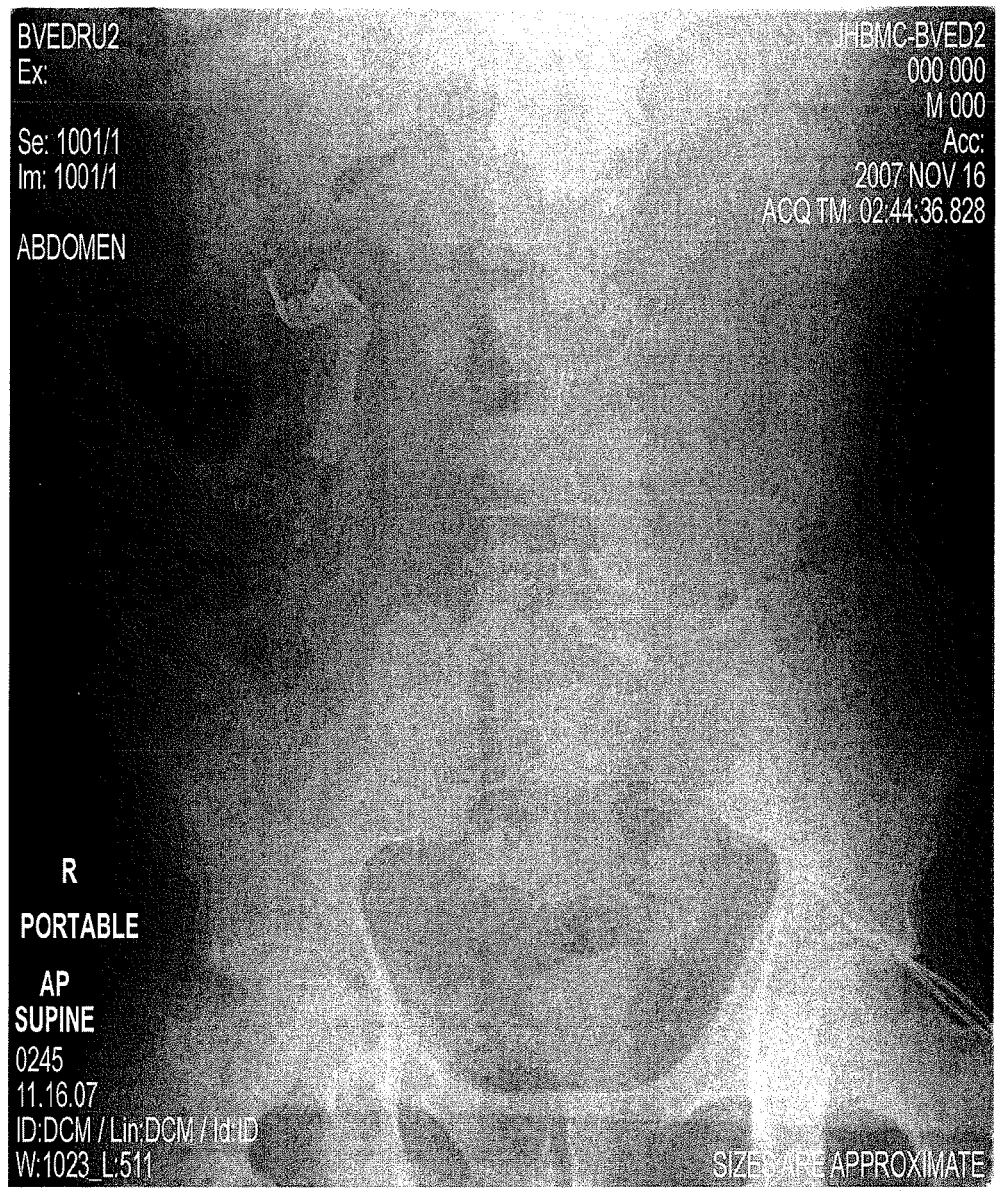
FIG. 3A shows an example of a portable X-ray image, cassette based.
Figure 3B:
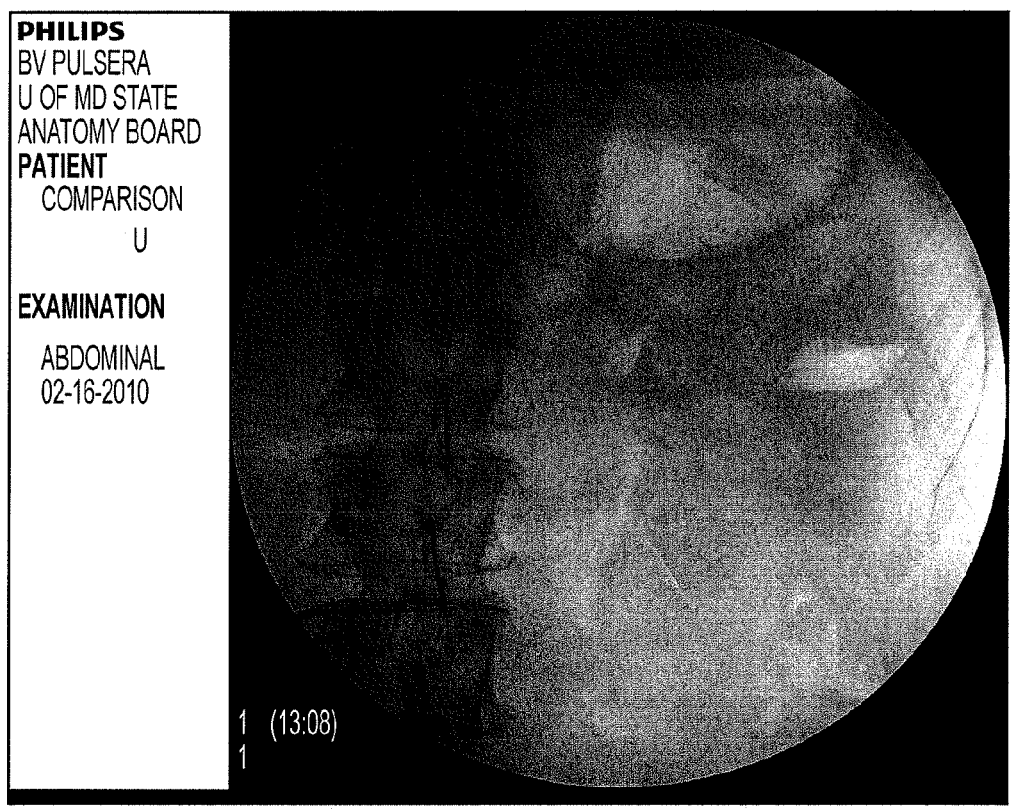
FIG. 3B shows an example of a C-arm, digital X-ray image.
Figure 4:
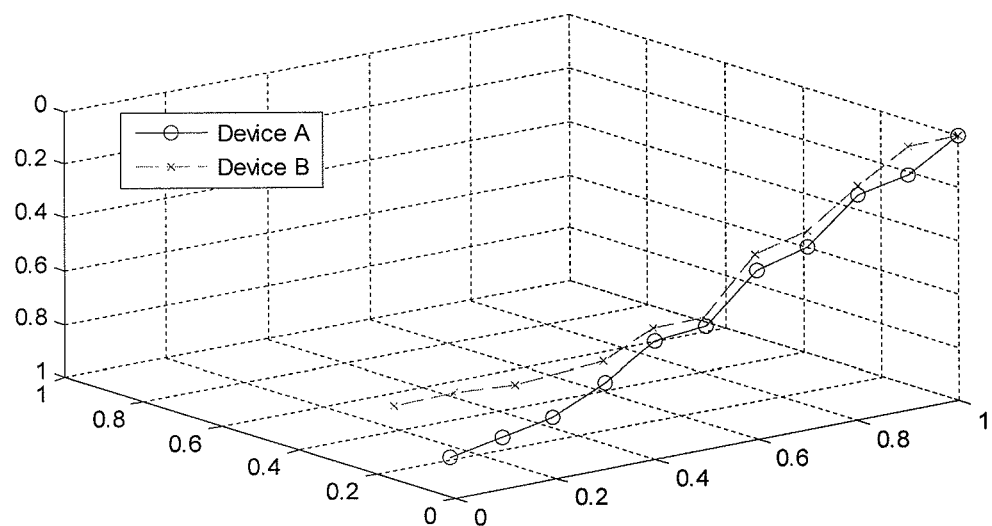
FIG. 4 provides the 3D ROC curves of Image A and Image B according to an embodiment of the current invention.

We used needles for this example. In order to demonstrate Modified-MSC (MMSC) according to an embodiment of the current invention, two different sets of X-ray images were used for experimental evaluation. These two sets of images were taken by two different X-ray machines. FIGS. 3A and 3B show both of the images. As mentioned in the previous section, the whole X-ray image was segmented into small pieces (sub-images) of the size 250×250 to detect needles. The window size could be adjusted to adapt to the size of needle inside the image. Table I tabulates the number of images used to evaluate our algorithm. There are 455 and 365 subimages with size 250×250 cropped from 60 and 60 X-ray images taken by device A (portable X-ray machine-cassette based) and B (C arm-digital). Image A comprises 54 subimages with needle and 401 without. Image B comprises 55 subimages with a needle inside and 300 without. These images were then inputted into the program which implements the modified MSC algorithm with a reference image. The output of the program is a scalar which indicates the possibility to have a needle inside the input image compared to the reference image. Two thresholds, $\tau$, were empirically chosen for the following evaluation. If the output scalar is larger than the chosen threshold, then we consider that there is a least a needle detected in the input image. Table II shows the results with $\tau=0$ and Table III shows the ones with $\tau=0.5$. Table IV tabulates the detection and false alarm rate of these two thresholds. FIG. 4 shows the 3D ROC curves on both devices.

TABLE I

The images used for the experiments

|  | With a needle | Without needle |
|---|---|---|
| Image A | 54 | 401 |
| Image B | 55 | 300 |

TABLE II

The detection result from the algorithm when $\tau = 0$.

|  |  | True positive | True negative |
|---|---|---|---|
| Image A | Positive detection | 46 | 4 |
|  | Negative detection | 8 | 397 |
| Image B | Positive detection | 40 | 47 |
|  | Negative detection | 15 | 253 |

TABLE III

The detection result from the algorithm when $\tau = 0.5$.

|  |  | True positive | True negative |
|---|---|---|---|
| Image A | Positive detection | 29 | 0 |
|  | Negative detection | 25 | 401 |
| Image B | Positive detection | 28 | 2 |
|  | Negative detection | 27 | 298 |

TABLE IV

The detection and false alarm rate of two thresholds.

|  |  | Detection rate | False alarm rate |
|---|---|---|---|
| Image A | $\tau = 0$ | 85.19% | 9.98% |
|  | $\tau = 0.5$ | 53.70% | 0.00% |
| Image B | $\tau = 0$ | 72.73% | 15.67% |
|  | $\tau = 0.5$ | 50.91% | 6.67% |

Results

The automated detection rate was up to 70-86% with false alarm (false positive) from 10-15% when $\tau$ was zero. In other words, the detection rate was up to 86% without human interpretation.

Discussion

RFB are a recalcitrant problem. Estimates indicate that it is quite rare. It was not always thus. Various interventions that we have instituted through the years have resulted in improved out comes. They have also resulted in a paradigm shift about the approach to this problem in modern times.

Some of the earliest reports of intervention to prevent RFB date back to 1901. Schachner detailed the prophylactic measure of counting. Time to detection of RFB was increased when the count was introduced; however, neither counting nor tagging of equipment (also reported in 1901) resulted in significant decrease in mortality and morbidity though they reportedly decreased the incidence of RFB. Subsequently, X-rays were introduced as a technology that could reduce the incidence of RFB in the 1940's. X-rays increased the time of the process (including setting up to do the X-ray, developing the X-ray and reading the X-ray) but again did not significantly improve accuracy or decrease significantly the mortality and morbidity from previous reports.

In order to improve the accuracy of detection of RFB, there had to be an improvement in the technology used to identify RFB and there also had to be accommodation in the system: technology combined with accommodation (TCA), exemplified by the switch to radio-opaque sponges (accommodation of the system) that lead to a dramatic decrease in mortality and morbidity rates due to more accurate detection. The system changed to manufacture and purchase, disposable, radio opaque sponges so that they could be better visualized on X-ray. This was no small investment but radio opaque sponges decreased mortality and morbidity and incidence while increasing accuracy of detection without increasing the time spent in detecting RFBs.

In the 1990's, with the publication of the Institute of medicines landmark paper "To Err is Human", optimization of all the above techniques, processes and culture took place resulting in RFBs becoming extremely rare. The rate is estimated to be 1 in 5500 when you carry out X-rays on all patients.

Optimization involves improvement of all the above described technologies (count, X-ray, digital radiological equipment and improvement of X-ray portable machines as well as standardized guidelines for prevention of RFB from ACS and AORN, reporting processes, and patient safety initiatives). That has had the effect of possibly even decreasing further RFB incidence. The effect of this is that the paradigm has shifted; we now have the luxury of considering technologies that impact not only the incidence of RFB but also the time to detection and accuracy of detection of ALL (instruments, needles as well as sponges) RFBs.

Currently, automated data identification tags (ADIC) have been proposed to be used to detect RFBs e.g. bar codes and Radiofrequency (RFID) tags. This technology is based on the TCA premise, technology (ADIC tags) combined with accommodation of the system (changes in the system to manufacture and purchase special disposable sponges). The technology would have been an excellent choice in the 1950-70's where it would have had, no doubt, a huge decrease in the incidence, mortality and morbidity while increasing accuracy. Obviously the time to detection would be increased (TCA based technologies do not decrease the necessity for X-rays in 81% of cases) so X-rays would have been ordered in any case, when indicated, independent of the presence of ADIC tag technology e.g. for surgery that has to performed as an emergency, incorrect instrument or needle count etc. and protocols will have to revised for equipment that cannot be tagged or sterilized. In the present, in addition to all these disadvantages, this is an enormous cost: both directly financial as well as cost in terms of the new resources that would have to be put in place. Finally, in their current iteration, TCA based technologies have not solved the problem of the human factor (for example the RFID wand—the RFID tags are read by wands-still has to be operated by humans); thus they may not impact patient safety, currently, in clinical practice. The optimum time for benefitting from TCA based technologies has probably passed: TCA based technologies would've had a much larger impact on mortality and morbidity in the 1950-70's if it had been introduced instead of radio-opaque sponges.

CT is another technology that has been proposed to detect RFB. With this modality, the accuracy is increased; however, radiation injury and potential cancer are the consequence of using CT. In addition, it would increase the time to detection and radiologists have been known to miss RFB on CT.

The potential advantages of the method described in this embodiment of the current invention would include the fact that this technology is a multi-perspective technology offering advantages that encompass time to detection, accuracy of detection as well as decreased incidence of leaving RFB in the body which directly impact the mortality and morbidity. A further advantage of some embodiments of the current invention is that it enhances the process of detection of a rare event: (RFB) by using automation to detect suspicious events which can then be read at a later time by the radiologist.

Machine learning applications can be ideally suited to the search for RFBs according to some embodiments of the current invention because the various types of RFBs are of constant shape and size, e.g., a sponge or a needle is the same wherever it is used in the world. In addition, multiple machine learning algorithms can be combined to optimize outcomes. Given that accuracy of needle detection falls when needles are small, due mainly to the inability to distinguish them from the surroundings, the proposed algorithm might be able to improve on the radiologists 30% detection rate for small needles (<10 mm).

Therefore, some salient features of Reference Map-Seeking Circuit (RMSC) according to some embodiments of the current invention can be summarized by the following three points. First, it allows the algorithm to complete the search with a single iteration while the conventional Map-Seeking Circuit (MSC) requires several iterations to reach a "Steady-state". Since most medical applications require an immediate response time, RMSC can meet this requirement to achieve real time or near real time performance in according with some embodiments of the current invention. Second, features of RFBs can be easily introduced by the reference images, a novel aspect of RMSC. The reference images contain features of RFBs because they have been chosen by specialists, such as doctors and/or radiologists. An embodiment of the current invention thus can bring the knowledge of doctors into the algorithm to further increase the detection rate. Third, the reference image can reduce device "noise" and allow for optimal search performance in accordance with some embodiments of the current invention. This is because the test and reference images can be taken from the same sensor. This can help reduce false alarms caused by device noise while increasing the detection rate. These features can lead to RMSC according to some embodiments of the current invention outperforming MSC in both detection rate and computational speed.

The embodiments illustrated and discussed in this specification are intended only to teach those skilled in the art how to make and use the invention and are not intended to define the scope of the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for detecting post-operative retained foreign bodies, comprising:
    a data storage unit adapted to receive and store a reference image of a surgical object; and
    a data processor in communication with said data storage unit,
    wherein said data processor is configured to receive an image of an internal region of a patient and to receive said reference image from said data storage unit, and
    wherein said data processor is configured to perform operations based on an algorithm to compare said reference image to at least a portion of said image of said internal region of said patient and determine whether a retained foreign body is present in said patient.

2. A system for detecting post-operative retained foreign bodies according to claim 1, further comprising an image acquisition system in communication with said data processor,
    wherein said image acquisition system is configured to obtain said image of said internal region of said patient and to transfer said image of said internal region to said data processor.

3. A system for detecting post-operative retained foreign bodies according to claim 1, wherein said reference image of said surgical object is a preselected reference image selected by an expert as having a characteristic appearance of said surgical object.

4. A system for detecting post-operative retained foreign bodies according to claim 1, wherein said data storage unit is adapted to receive and store a plurality of reference images of said surgical object,
    wherein said data processor is configured to receive said plurality of reference images from said data storage unit, and
    wherein said data processor is configured to perform operations based on an algorithm to compare said plurality of reference images to at least a portion of said image of said internal region of said patient and determine whether a retained foreign body is present in said patient.

5. A system for detecting post-operative retained foreign bodies according to claim 1, wherein said data processor is further configured to generate a plurality of internal images based on said image of said internal region of said patient by applying at least one of rotational, translational and scaling transformations to said image and comparing at least a portion of each of said plurality of internal images to said reference image.

6. A system for detecting post-operative retained foreign bodies according to claim 1, wherein said data processor is configured to determine whether said retained foreign body is present in said patient in real time during surgery.

7. A system for detecting post-operative retained foreign bodies according to claim 1, wherein said algorithm is a modified map-seeking circuit algorithm.

8. An automated method of detecting post-operative retained foreign bodies, comprising:
    storing a reference image of a surgical object in non-transient, digital form;

obtaining an image of an internal region of a patient in digital form;

retrieving said reference image and comparing, based on a computer algorithm, said reference image to at least a portion of said image of said internal region of said patient; and determining whether a retained foreign body is present in said patient based on said comparing said reference image of said surgical object to said at least a portion of said image of said internal region of said patient using said computer algorithm on a computer.

9. An automated method of detecting post-operative retained foreign bodies according to claim 8, wherein, prior to said storing, said reference image of said surgical object is selected by an expert as having a characteristic appearance of said surgical object.

10. An automated method of detecting post-operative retained foreign bodies according to claim 8, further comprising:

storing a plurality of reference images of said surgical object in non-transient, digital form;

retrieving said plurality of reference images and comparing, based on said computer algorithm, said plurality of reference images to at least said portion of said image of said internal region of said patient; and determining whether said retained foreign body is present in said patient based on said comparing said plurality of reference images of said surgical object to said at least said portion of said image of said internal region of said patient using said computer algorithm on said computer.

11. An automated method of detecting post-operative retained foreign bodies according to claim 10, wherein, prior to said storing said plurality of reference images of said surgical object, a characteristic image of said surgical object is selected by an expert as having a characteristic appearance of said surgical object.

12. An automated method of detecting post-operative retained foreign bodies according to claim 8, further comprising generating a plurality of internal images based on said image of said internal region of said patient by applying at least one of rotational, translational and scaling transformations to said image and comparing at least a portion of each of said plurality of internal images to said reference image.

13. An automated method of detecting post-operative retained foreign bodies according to claim 8, wherein said determining whether said retained foreign body is present in said patient is performed in real time during surgery.

14. An automated method of detecting post-operative retained foreign bodies according to claim 8, wherein said computer algorithm is a modified map-seeking circuit algorithm.

15. A non-transitory computer-readable medium comprising software, wherein, when executed by a computer, causes the computer to:

receive an image of an internal region of a patient; receive a reference image of a surgical object;

compare said reference image to at least a portion of said image of said internal region of said patient using a computer algorithm; and determine whether a retained foreign body is present in said patient based on said comparing said reference image of said surgical object to said at least a portion of said image of said internal region of said patient using said computer algorithm.

16. A non-transitory computer-readable medium according to claim 15, wherein said reference image of said surgical object is a preselected image selected by an expert as having a characteristic appearance of said surgical object.

17. A non-transitory computer-readable medium according to claim 15, wherein said computer is further caused to: receive a plurality of reference images and compare said plurality of reference images to at least said portion of said image of said internal region of said patient; and determine whether said retained foreign body is present in said patient based on said comparing said plurality of reference images of said surgical object to said at least said portion of said image of said internal region of said patient.

18. A non-transitory computer-readable medium according to claim 15, wherein said computer is further caused to generate a plurality of internal images based on said image of said internal region of said patient by applying at least one of rotational, translational and scaling transformations to said image and comparing at least a portion of each of said plurality of internal images to said reference image.

19. A non-transitory computer-readable medium according to claim 15, wherein said computer is further caused to determine whether said retained foreign body is present in said patient in real time during surgery.

20. A non-transitory computer-readable medium according to claim 15, wherein said computer algorithm is a modified map-seeking circuit algorithm.

* * * * *